United States Patent
Okada

(10) Patent No.: US 6,558,406 B2
(45) Date of Patent: May 6, 2003

(54) VEIN FILTER

(75) Inventor: Masayosi Okada, Osaka (JP)

(73) Assignee: Nipro Corporation, Osaka (JP)

( * ) Notice: Subject to any disclaimer, the term of this patent is extended or adjusted under 35 U.S.C. 154(b) by 112 days.

(21) Appl. No.: 09/812,679

(22) Filed: Mar. 21, 2001

(65) Prior Publication Data
US 2001/0025187 A1 Sep. 27, 2001

(30) Foreign Application Priority Data
Mar. 23, 2000 (JP) ........................................ 2000-081352

(51) Int. Cl.$^7$ ............................................. A61M 29/00
(52) U.S. Cl. ........................................................ 606/200
(58) Field of Search ................................ 606/200, 198, 606/191, 199, 194, 159, 113, 110, 158; 604/53, 104, 105, 106, 107, 108

(56) References Cited

U.S. PATENT DOCUMENTS

| | | | |
|---|---|---|---|
| 4,643,184 A | | 2/1987 | Mobin-Uddin .......... 128/303 R |
| 4,793,348 A | | 12/1988 | Palmaz ...................... 128/325 |
| 5,234,458 A | * | 8/1993 | Metais ........................ 606/200 |
| 5,375,612 A | * | 12/1994 | Cottenceau et al. ........ 128/899 |
| 5,683,411 A | * | 11/1997 | Kavteladze et al. ........ 606/200 |
| 5,941,896 A | * | 8/1999 | Kerr ............................ 606/200 |
| 5,954,742 A | * | 9/1999 | Osypka ....................... 606/198 |
| 6,193,739 B1 | * | 2/2001 | Chevillon et al. .......... 606/200 |
| 6,231,589 B1 | * | 5/2001 | Wessman et al. .......... 606/200 |
| 6,273,900 B1 | * | 8/2001 | Nott et al. .................. 606/200 |
| 6,273,901 B1 | * | 8/2001 | Whitcher et al. ........... 606/200 |

* cited by examiner

Primary Examiner—Gloria M. Hale
Assistant Examiner—Alissa L Hoey
(74) Attorney, Agent, or Firm—Kubovcik & Kubovcik

(57) ABSTRACT

A vein filter having improved collectability of chyme blood or thrombi and stability of indwelling. The filter includes at least 3 wires radially spreading backward of a head member and connected such that the intervals between any adjacent two wires are connected with threads of an equal length at a substantially equal distance from the head member. At respective connection parts where the threads are connected to the wires, hook parts to be hooked on the inner wall of a blood vessel are provided. The head member is on the apex of a shaft extending back and the rear end of each wire is connected to a slide member slidable along the shaft. The wires are preferably made of shape memory alloy or stainless spring steel.

4 Claims, 8 Drawing Sheets

VEIN FILTER

FIELD OF THE INVENTION

The present invention relates to a vein filter for preventing pulmonary infarction and which is mainly indwelt in the inferior caval vein.

DESCRIPTION OF THE RELATED ART

Recently, as the number of elderly persons of advanced age has increased in society, more attention has been paid to an increase in vein diseases as well as to an increase in arterial sclerosis. Vein diseases have not been given as much importance as arterial diseases. However, high attention has recently come to be paid to their importance. This is because when deep vein thrombosis occurs, a part of it is released and flows into the pulmonary artery to induce thromboembolism of the pulmonary artery, and as a result severe respiratory failure is caused. Once pulmonary artery thromboembolism occurs, the prognosis in many cases is very poor and there is a high risk of death unless an effective therapeutic means is applied.

Therefore, to forestall pulmonary artery thromboembolism, a vein filter has been indwelt in the inferior caval vein in order to collect chyme blood or thrombi, which occurs on the side of the lower extremities. However, conventional filters having wires constructed in the form of a framework of an umbrella which can open in a conical shape have the problem that since the respective wires are not restricted and move freely, the distances between adjacent wires are not always the same, with the result that a broad gap may be formed between wires and chyme blood or thrombi cannot be sufficiently collected. Another problem is that the distances between adjacent wires may be uneven and cause the conical shape to deform. This results in the filter tending to be indwelt in the vein obliquely and unstably so that it tends to move toward the proximal portion of the inferior caval vein and is difficult to maintain in a predetermined position. Furthermore, it is difficult to adjust the pressure at which the wires contact the inner wall of the vein and problems occurs in that too strong a pressure results in constriction or injury of the inner wall and too weak a pressure fails to give stable anchorage.

Accordingly, in view of the above problems of the prior art, the present inventors have made extensive research with respect to a vein filter in which the distances between wires are made equivalent to increase the collectability of chyme blood or thrombi and to improve the stability of the filter when indwelt and as a result they have achieved the present invention.

SUMMARY OF THE INVENTION

The present invention is a vein filter which comprises a head member, at least three wires of equivalent length, the wires having front ends fixed to the head member, the wires extending radially from the head member backward, a connection part comprising threads of substantially equivalent length, each connecting two adjacent wires at a position an equivalent distance from the head member, and a hook part provided on the connection part for hooking onto an inner wall of a blood vessel to fix the filter.

Further, the present invention is a vein filter which further comprises a shaft having a front end at which the head member is provided and a slide member slidable along the shaft, wherein the wires have rear ends connected to the slide member.

Furthermore, the present invention is a vein filter in which the wires comprise a shape memory alloy or a stainless spring steel.

DETAILED DESCRIPTION OF THE INVENTION

As used herein, "forward" means the direction toward the head member 12 and "backward" means the direction departing from the head member 12.

Next, embodiments of the vein filter of the present invention will be described in detail with reference to the drawings.

Figure 1:
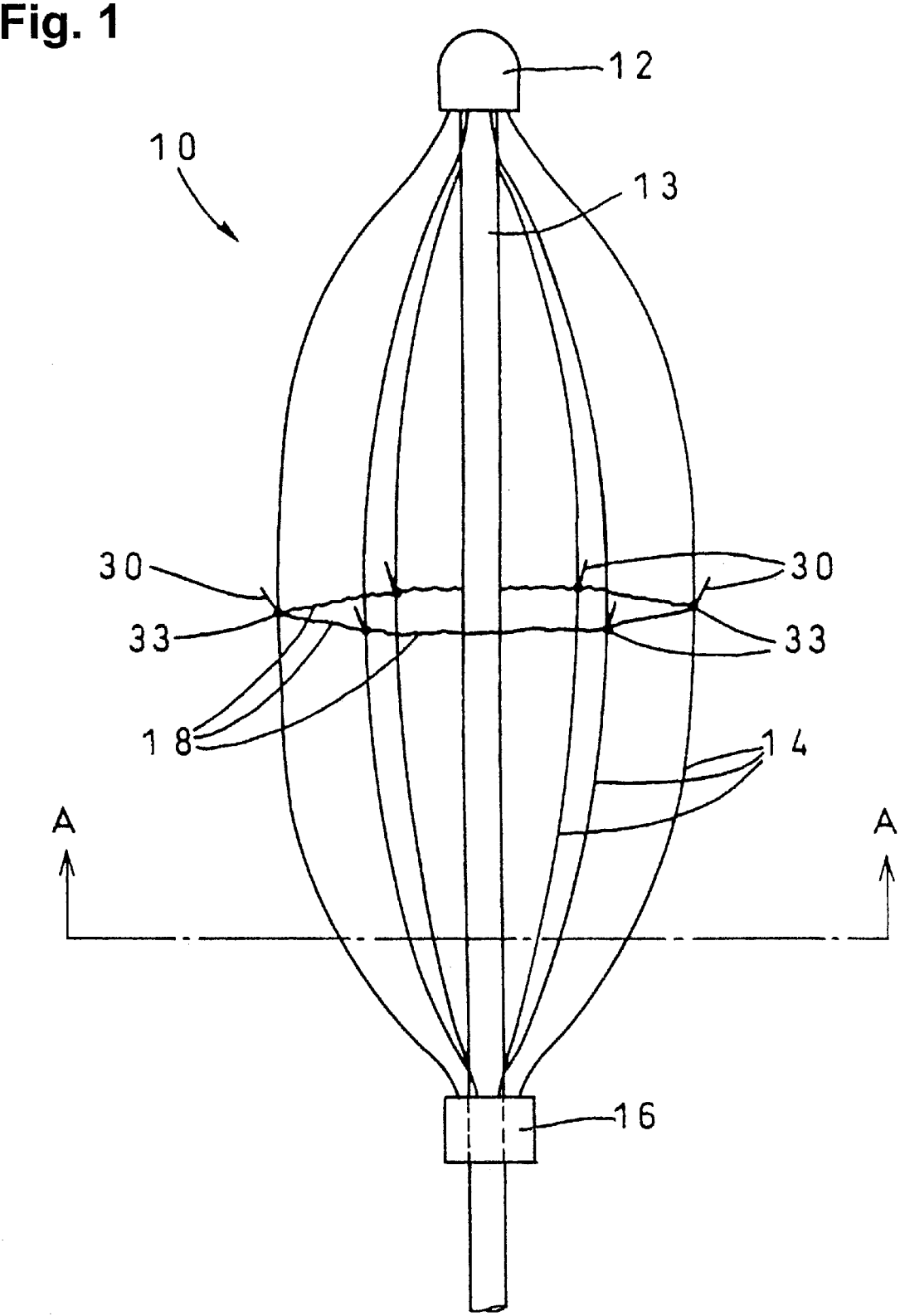
FIG. 1 is a perspective view showing an embodiment of the vein filter of the present invention
Figure 2:
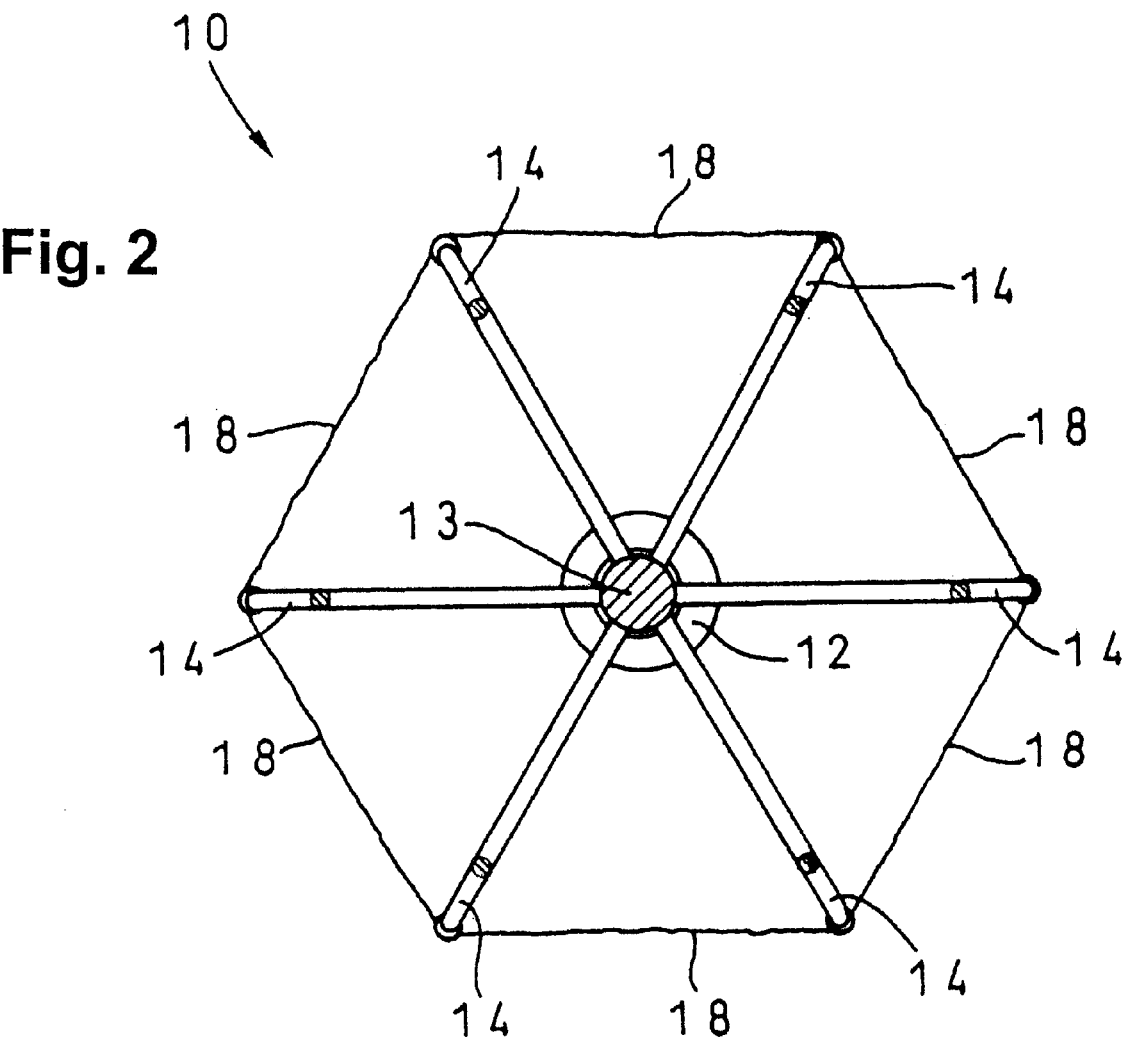
FIG. 2 is a cross-sectional view of the vein filter of the present invention along the line A—A in FIG. 1.

FIG. 1 is a perspective view showing a preferred embodiment of the vein filter of the present invention. FIG. 2 is a cross-sectional view along the line A—A of FIG. 1. A vein filter 10 comprises a head member 12, an annular slide member 16, a shaft 13 which extends backward from the head member 12 and slidable penetrates and moves through a circular hole in the slide member 16 six wires 14 each having the same length, and six threads 18 each having the same length. Each wire 14 has a front end fixed the head member 12 and a rear end fixed to the slide member 16 and is bent in an arcuate form, thus forming as a whole a cylindrical or conical vein filter 10. Adjacent wires 14 are connected with each other by one of the threads 18 of substantially the same length at positions the same distance from the head member 12, so that the six threads 18 form a regular hexagon. At respective connection parts 33 connecting wires 14 with threads 18 hook parts 30 are provided for hooking onto the inner wall of blood vessel to anchor the vein filter 10 in the inside of a blood vessel. The diameter or thickness of the hook parts 30 is preferably on the order of 0.1 mm to 0.3 mm. The length of the hook parts 30 is preferably on the order of 0.3 mm to 1.0 mm. The hook parts 30 can be attached to connection parts 33 extending outwardly from the wires 14 by welding onto the connection parts 33 or by bending and cutting a knot of the wires 14.

Figure 3:
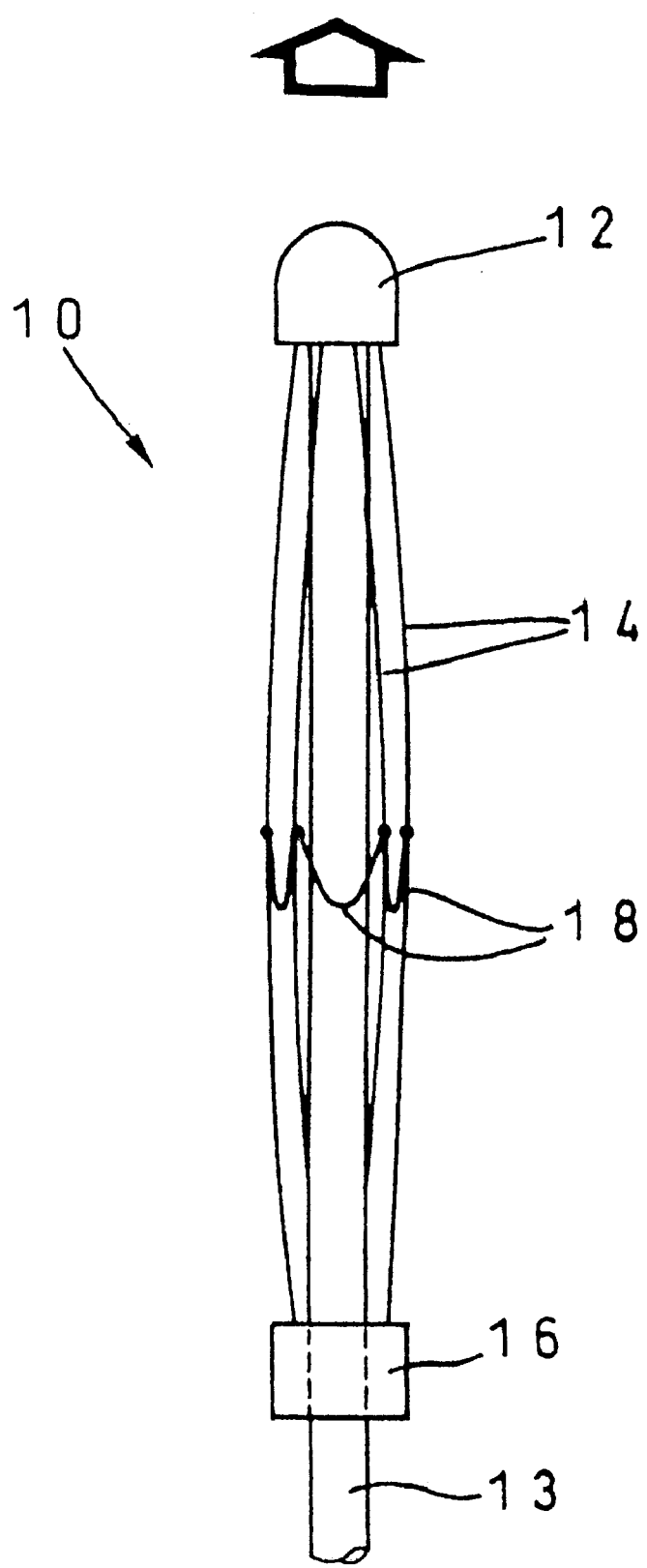
FIG. 3 is a side view of the vein filter of the present invention, shown in FIG. 1, in a closed state.

FIG. 3 illustrates the vein filter 10 switched from the state in which it is in a cylindrical or conical open form as illustrated in FIG. 1 into the state where it is in a closed form like a rod. That is, the retreat of the slide member 16 backward along the shaft 13 pulls the rear ends of the wires 14 to correct the arcuate bent state such that the wires are elongated in a form of a relatively straight line until they become substantially parallel with the shaft 13. At the same time, as the respective wires 14 come closer to each other, the flexible threads 18 which had been fully elongated between the wires 14 are relaxed and folded. As a result, all of the wires 14 and threads 18 gather around the shaft 13 and, as a whole, form the substantially rod-shaped vein filter 10.

Figure 4A:
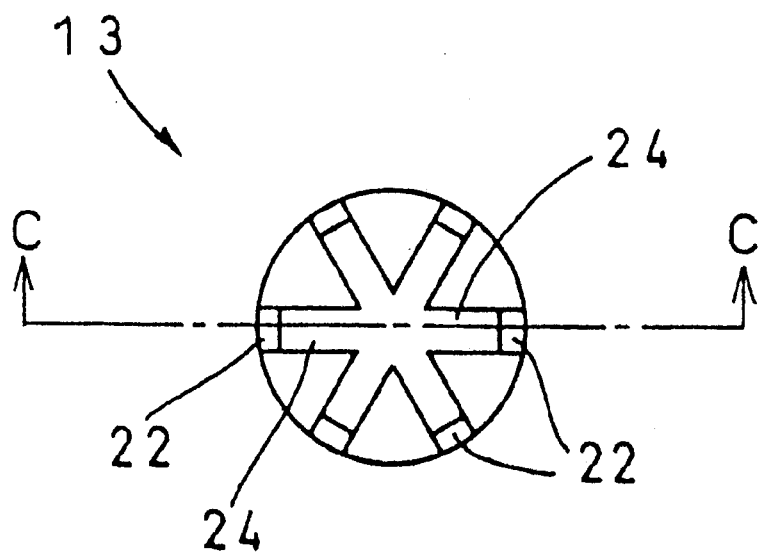
FIGS. 4(a) and 4(b) illustrate an enlarged view of an apex portion of a shaft of the vein filter of the present invention shown in FIG. 1, with FIG. 4(a) being a top view and FIG. 4(b) being a longitudinal cross-sectional view along the line C—C.
Figure 4B:
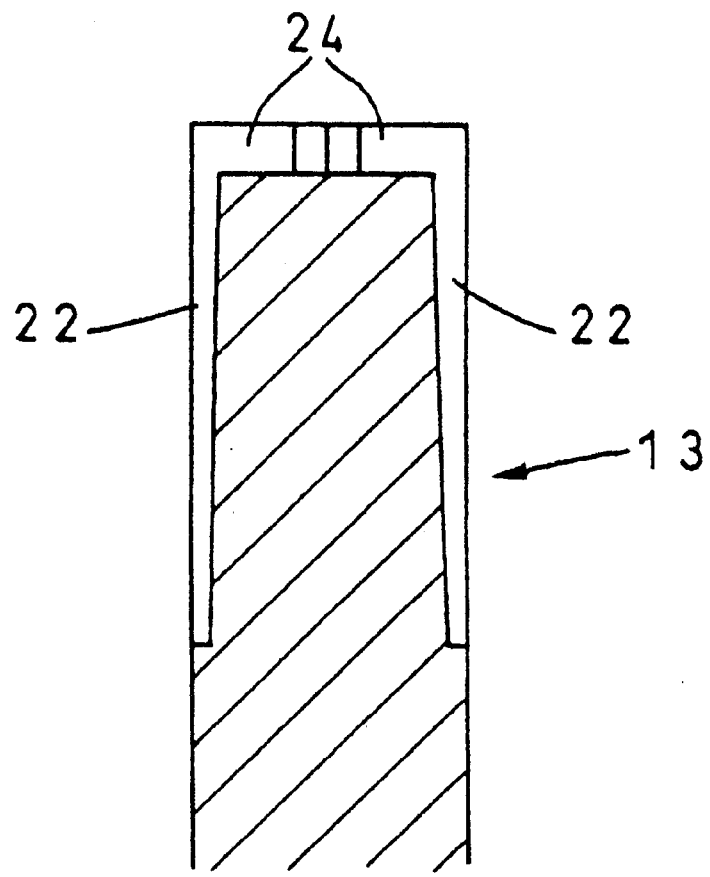
Figure 5A:
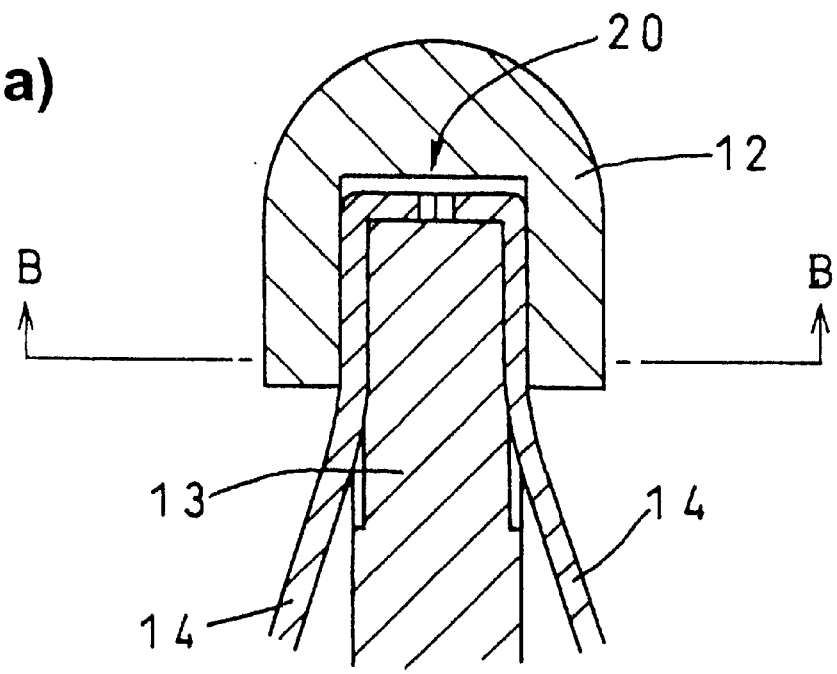
FIGS. 5(a) and 5(b) illustrate the circumference of the head member of the vein filter of the present invention shown in FIG. 1, with FIG. 5(a) being a longitudinal cross-sectional view and FIG. 5(b) being a horizontal cross-sectional view along the line B—B.
Figure 5B:
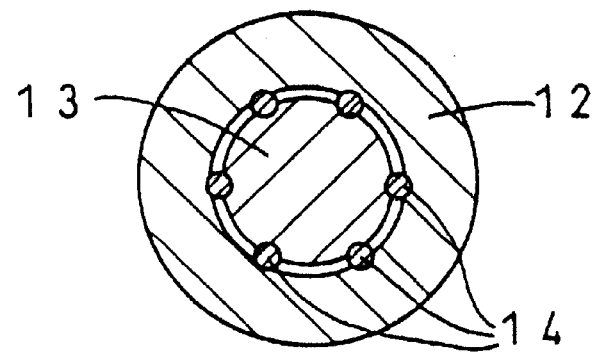

FIG. 4 shows a front end, or the tip portion, of the shaft 13. FIG. 5 shows the structure around the head member 12. On the tip of the front end the shaft 13 is provided with grooves 24 in the form of * and around the front end is provided with six grooves 22 formed by an extended portion of the groove 24 folded along the side surface. The head member 12 is provided with a frustoconical hole 20 with a gentle slope, in which the front end of the shaft 13 and the front ends of the six wires 14 are inserted for fitting and fixing. The wires 14, of which the front ends are bent in the form of L, are fitted in the grooves 24 and 22 in advance and then the shaft 13 and six wires are together inserted into the frustoconical hole 20 of the head member 12 and fitted. Temporary fixation of the wires 14 to the shaft 13 with adhesive makes it easy to perform the operation and thus is convenient.

The respective wires 14 are positioned at predetermined locations symmetrically around the shaft 13 by the grooves 22 and their rotation is suppressed by the groove 24 so that they are controlled to warp out in the direction that they depart from the shaft 13. It is an inevitable condition for the vein filter 10 to be opened in a cylindrical or conical form that the respective wires 14 are arranged symmetrically around the shaft 13 and warp out in the direction that they depart from the shaft 13.

Figure 6A:
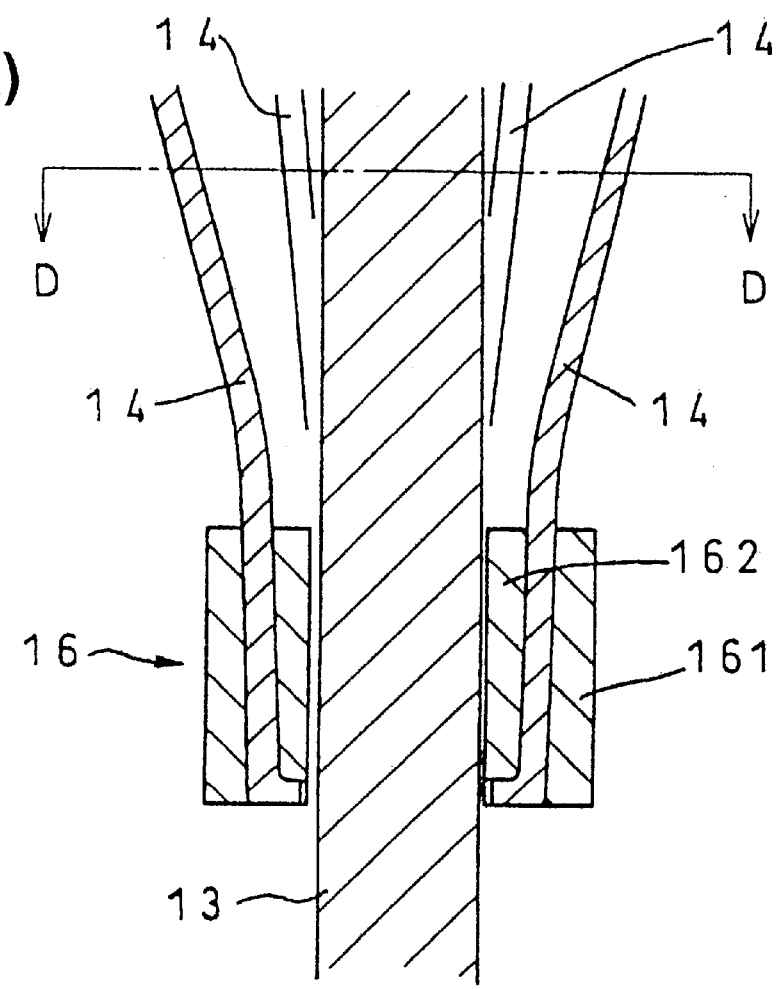
FIGS. 6(a) and 6(b) illustrate an enlarged view of the circumference of the slide member of the vein filter shown in FIG. 1, with FIG. 6(a) being a longitudinal cross-sectional view and FIG. 6(b) being a horizontal cross-sectional view.
Figure 6B:
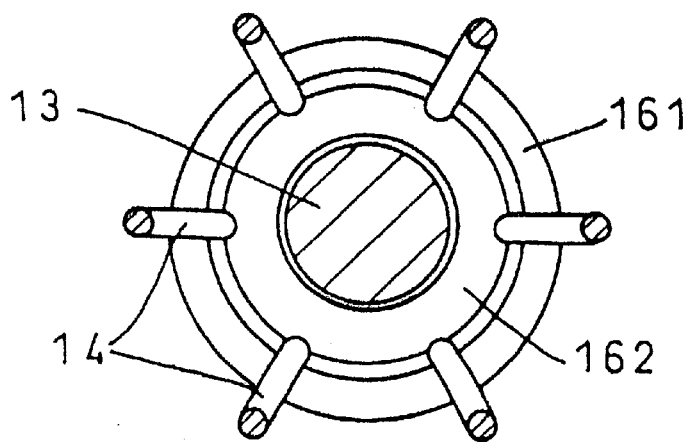

FIG. 6 shows the structure around the slide member 16. The slide member 16 is made of a double construction, which comprises an outer member 161 of an annular form and an inner member 162 also of an annular form inserted therein, and between which the wires 14 are inserted to fix them. In a manner similar to the tip portion of the shaft 13, a groove 26 in the form of * is provided on the bottom of the inner member 162 and six grooves 28 constituted by extended and folded portions of the groove 26 are provided along the outer side surface of the inner member 162. The wires with their rear end bent in the form of an L are fitted in the grooves 26 and 28 in advance and the inner member 162 and the six wires 14 are together inserted into the outer member 161 for fitting and fixing.

The vein filter 10 of the present invention is used as follows. First, a catheter is introduced percutaneously to a predetermined position where the vein filter 10 is to be indwelt in the inferior caval vein. Then, the vein filter 10 closed in a rod-shape as shown in FIG. 3 is inserted through the catheter to the position where it is to be indwelt with the head member 12 leading in the direction as shown by the arrow. The vein filter 10 pushed out of the catheter opens into a cylindrical or conical form automatically by bending of the wires 14 themselves or by having the slide member 16 advanced. On this occasion, the hook portions 30 provided at the connection parts 33 hook onto the inner wall of the blood vessel to anchor the vein filter 10. Anchoring by maintaining contact with the inner wall of the vein in a sufficiently opened state allows the vein filter 10 to be indwelt in the inside of the blood vessel stably without being moved away by the blood flow from behind.

In the vein filter 10 of the present invention, the wires 14 spreading radially backward of the head member 12 of the vein filter 10 are connected such that any two adjacent wires are connected with a thread 18 of the same length at a substantially equivalent distance from the head member 12 such that the intervals between the wires are maintained at an equal distance to make the cross section of the vein filter 10 a regular polygon. This allows the vein filter 10 to be indwelt while evenly contacting the cylindrical inner wall of a vein. Also, since the amount of bend of the wires 14 can be controlled by the length of the threads 18, the width of opening of the vein filter 10 can be adjusted to any desired size so that it can have a suitable size in accordance with the inner diameter of the vein at the position where indwelling is intended. As a result, drifting of the vein filter due to weak contact with the inner wall of a vein or too much contact of the filter with a vein, resulting in compression or injury of the inner wall of the vein, can be prevented. Also, uniform intervals between the wires 14 ensure that the filter will collect chyme blood or thrombi. Since the threads 18 are flexible, the vein filter 10 can be automatically folded when it is closed and moved in the catheter so that it does not hinder movement.

Further, in the vein filter 10 of the present invention, the rear end of each of wires 14 is fixed to the slide member 16 to make the vein filter 10 cylindrical or conical in shape so that the rear hemisphere and the front hemisphere both function as filters and considerably increase the collectability of chyme blood similar to a filter unit equipped with a coarse filter and a main filter. Since the rear end of each wire 14 is connected to the slide member 16 that is slidable along the shaft 13, the slide member 16 is retracted in order to close the vein filter 10. The hook parts 30 are released from the inner wall of the blood vessel by closing the vein filter 10. And the vein filter 10 can be removed from the body. The means by which the slide member 16 is forwarded or retracted is not particularly limited and various means can be adopted according to conventional methods. The slide member 16 may be modified, if necessary. The shaft 13 maybe made to have a length slightly greater than the wires 14 or may be extended to the outside of the body.

When in use, the vein filter 10 of the present invention is indwelt mainly in the inferior caval vein. However, it may also be used in the common iliac vein, the cervical vein, etc. Its size is not particularly limited but is preferably on the order of 40 mm to 50 mm in length and 17 mm to 20 mm in diameter when it is indwelt in inferior caval vein. The diameter, or thickness, in a closed state is preferably 3 mm or less taking into account the mobility in catheters.

The wires 14 are at least 3, and preferably 4 to 8, in number. The intervals between the wires 14 are preferably adjusted to 5 mm to 6 mm. If the intervals are too small, blood flow is inhibited while, if it is too broad, the collection of chyme blood or thrombi is insufficient. Neither is desirable. The wires 14 maybe circular in cross section or flat in cross section and ribbon-like. Their diameter or thickness is preferably on the order of 0.3 mm to 0.5 mm.

The wires 14 and hooks 30 may be made of any material as far as the material is biologically inactive and has stiffness and strength sufficient for maintaining the shape while they are indwelt in the vein and is not particularly limited. However, resilient materials and shape memory materials are preferably used. Use of a resilient material preliminarily set to the shape in which the vein filter 10 is in an open form will allow elastic recovery when it is pushed out of the catheter into a vein so that the vein filter 10 can automatically open. If use is made of a shape memory material which memorizes an open form of the vein filter 10 and returns to the memorized shape at or about body temperature, the vein filter 10 can be cooled to a rod-like form while it is being passed through the catheter and automatically opened by returning to the memorized shape when it is pushed out of the catheter into the vein and its temperature is elevated to near body temperature. Stainless spring steel is particularly preferred as the resilient material and a shape memory alloy such as Nichinol, the trade name of an alloy (manufactured by Bird Co., Ltd.) is particularly preferred as the shape memory material since they are excellent in corrosion resistance and mechanical properties. Where the wires 14 themselves are not imparted with the properties for opening the vein filter 10, the vein filter 10 can be forcibly opened by sliding the slide member 16 back and forth. Each of the wires 14 does not have to be constituted by a single seamless wire but it may be constituted by connecting two wires.

As the flexible thread, filament yarns or spun yarns made of metals or organic materials of 0.3 mm to 0.5 mm in diameter or thickness are used. Single yarns and twisted yarns made of filaments are used preferably since they are excellent in strength and flexibility. Threads having enough flexibility for them to be connected by tying them are particularly preferred.

In the foregoing, the description has been made based on the vein filter 10 illustrated in FIG. 1. However, the present invention is not limited to the above embodiment and may be embodied in various forms.

Figure 7:
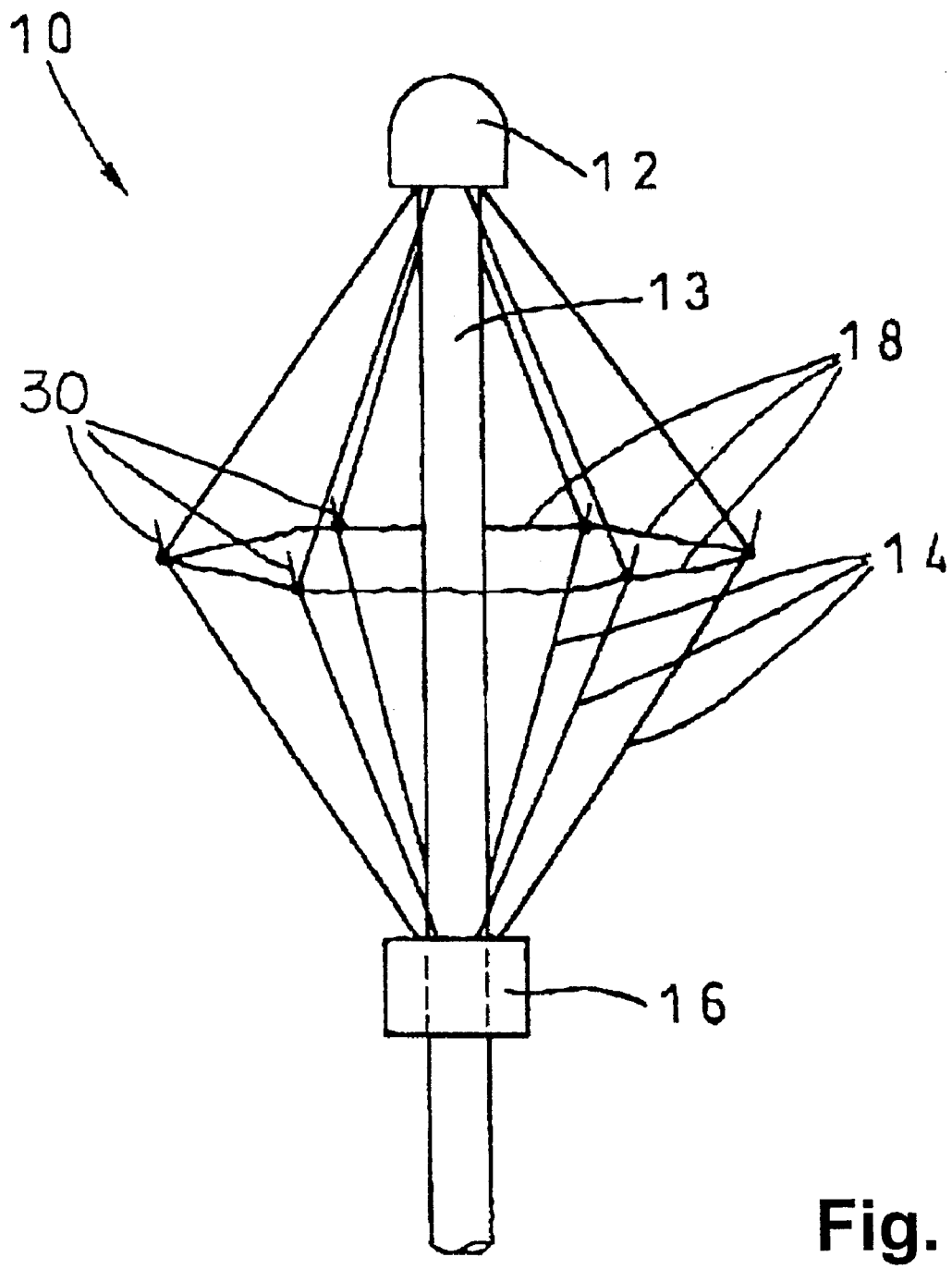
FIG. 7 is a perspective view showing another embodiment of the vein filter of the present invention.

For example, the vein filter 10 shown in FIG. 7 is provided with characteristics ensuring anchorage on the inner wall of a vein. That is, in the vein filter 10 as shown in FIG. 7, the wires 14 are bent in the form of the letter V so that a contact portion for contacting the inner wall of a vein has an angled form and anchorage can be increased.

Figure 8:
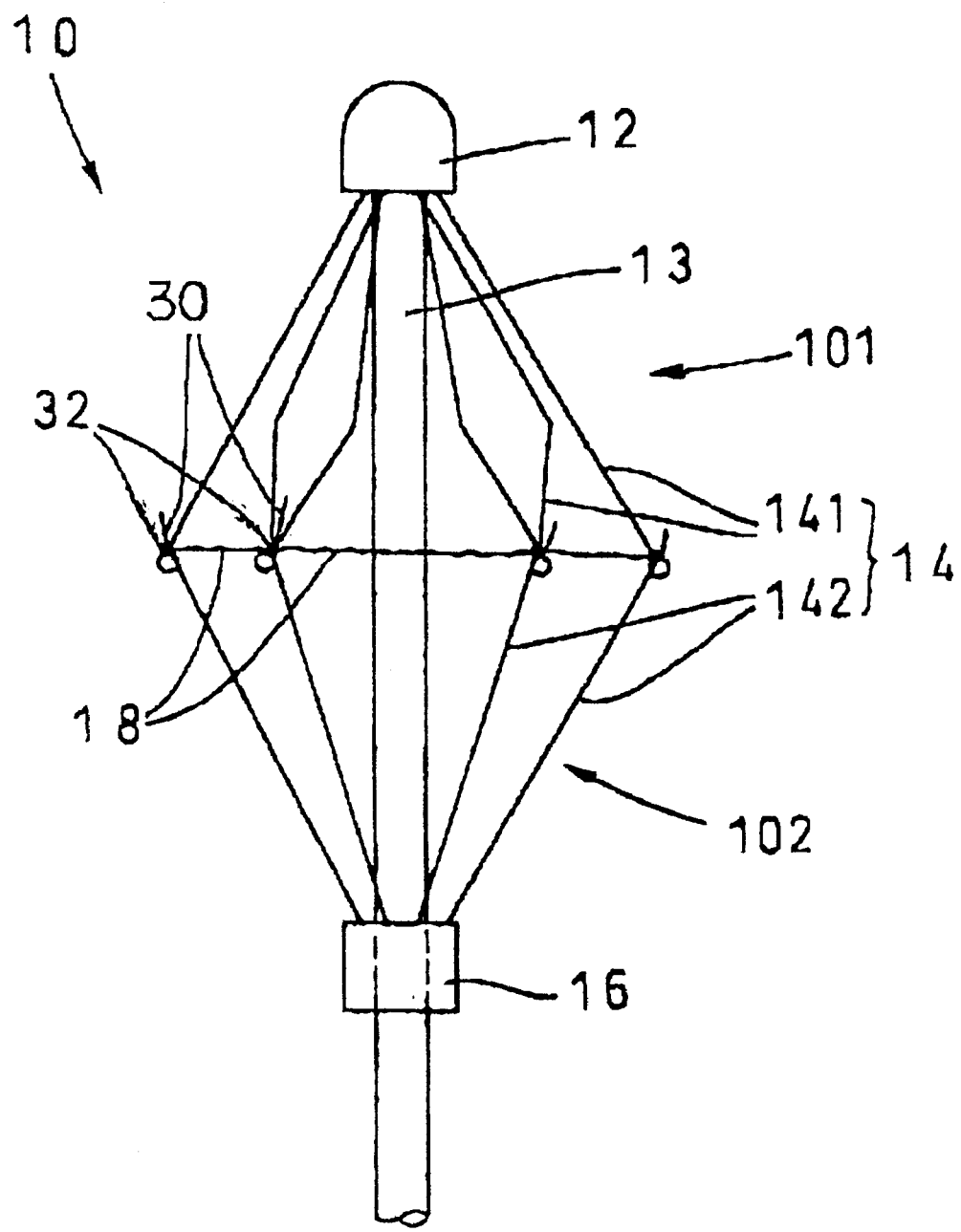
FIG. 8 is a perspective view showing another embodiment of the vein filter of the present invention.

In the vein filter 10 shown in FIG. 8, the wires 14 are constituted by front part wires 141 and rear part wires 142 connected to each other. The front part wires 141 are bent in the form of the contour of a necktie and the tip ends of front part wires 141 are fixed to the head 12. The back ends of front part wires 141 are rotatably connected to the tip ends of rear part wires 142 at the interconnected parts 32. As a result, the intervals between the wires 14 at the front part 101 of the vein filter 10 become narrower to further enhance the function of the vein filter as a double filter composed of the rear part filter 102 as a rough filter and the front part 101 as a main filter.

As described above, making the vein filter 10 in cylindrical or conical or the like shape by connecting the rear ends of the wires 14 to the slide member 16 adds the function of a double filter thereto. Also, since the vein filter 10 can be opened and closed by sliding the slide member 16 back and forth so that the vein filter 10 can be taken out of the body, it can be used as a temporary filter for a certain period. Therefore, this embodiment is particularly useful and adopted preferably.

The present invention can be practiced in embodiments with various improvements, modifications, or variations on the construction and shape of the vein filter, the material and shape of the wires, the material and attachment method of the thread, the driving method of the slide member and the like.

According to the construction of the vein filter of the present invention, any two adjacent wires are connected to each other through threads of equal length so that the intervals between the wires can be maintained at an equal distance to form a vein filter having a regular polygonal cross section. This allows the vein filter 10 to be indwelt while evenly contacting the cylindrical inner wall of a vein. Also, the length of the thread can regulate the amount of bend and the width of opening of the vein filter can be appropriately controlled in accordance with the thickness of the vein at a position where indwelling is intended. As a result, the intervals between the wires are uniform so that the collection of chyme blood or thrombi can be ensured. Furthermore, since the thread is flexible, the vein filter when it is moved in a catheter in a closed state is automatically folded and will not prevent movement.

Further, such a vein filter functions as a double filter when the rear end of each wire is fixed to the slide member, since the rear part and the front part, respectively, function as a rough filter and a main filter, resulting in a considerable increase in the collectability of chyme blood or thrombi. In addition, the vein filter can be taken out of the body by retracting the slide member to close the vein filter and release the hook parts from the inner wall of the vein.

Furthermore, in such a vein filter, use of wires made of stainless spring steel or shape memory alloy, which is excellent in corrosion resistance and mechanical strength, increases the durability of the filter, and enables it to automatically recover the preset shape so that the structure can be simplified and its fitting is easier.

What is claimed is:

1. A vein filter comprising a head member, at least three wires of equal length, said wires having front ends fixed to said head member, and extending radially from said head member backward, a connection part comprising threads of substantially equal length, each thread connecting two adjacent wires at a position an equal distance from said head member, and a hook means provided at each connection between a thread and wire for hooking onto an inner wall of a blood vessel to fix the filter.

2. The vein filter as claimed in claim 1, further comprising a shaft having a front end at which said head member is provided and a slide member slidable along said shaft, wherein said wires have rear ends connected to said slide member.

3. The vein filter as claimed in claim 2, wherein said wires comprises shape memory alloy or stainless spring steel.

4. The vein filter as claimed in claim 1, wherein said wires comprises shape memory alloy or stainless spring steel.

* * * * *